US00PP27926P3

(12) United States Plant Patent

De Wit et al.

(10) Patent No.: US PP27,926 P3
(45) Date of Patent: Apr. 25, 2017

(54) APPLE TREE NAMED 'KIZURI'

(50) Latin Name: ***Malus domestica* Borkh.**
Varietal Denomination: KIZURI

(71) Applicant: BETTER3FRUIT, N.V., Heverlee (BE)

(72) Inventors: Inge De Wit, Lovenjoel (BE); Hendrik Eyssen, Holsbeek (BE); Johan Keulemans, Korbeek-Lo (BE); Johan Nicolaï, Sint-Truiden (BE); Paul Van Laer, Heks (BE)

(73) Assignee: Better3Fruit, N.V., Heverlee (BE)

( * ) Notice: Subject to any disclaimer, the term of this patent is extended or adjusted under 35 U.S.C. 154(b) by 0 days.

(21) Appl. No.: 14/757,271

(22) Filed: Dec. 11, 2015

(65) Prior Publication Data

US 2016/0174428 P1 Jun. 16, 2016

(30) Foreign Application Priority Data

Dec. 15, 2014 (QZ) ..... PBR 2014/3424

(51) Int. Cl.
*A01H 5/08* (2006.01)

(52) U.S. Cl.
USPC ..... Plt./161

(58) Field of Classification Search
USPC ..... Plt./161
See application file for complete search history.

*Primary Examiner* — Annette Para
(74) *Attorney, Agent, or Firm* — Foley & Lardner LLP

(57) ABSTRACT

A new and distinct variety of *Malus domestica* apple tree named 'KIZURI', particularly characterized by very aromatic and sweet fruit with a solid, vibrant red flush, very firm with dense texture and very good storability.

9 Drawing Sheets

Figure 1:
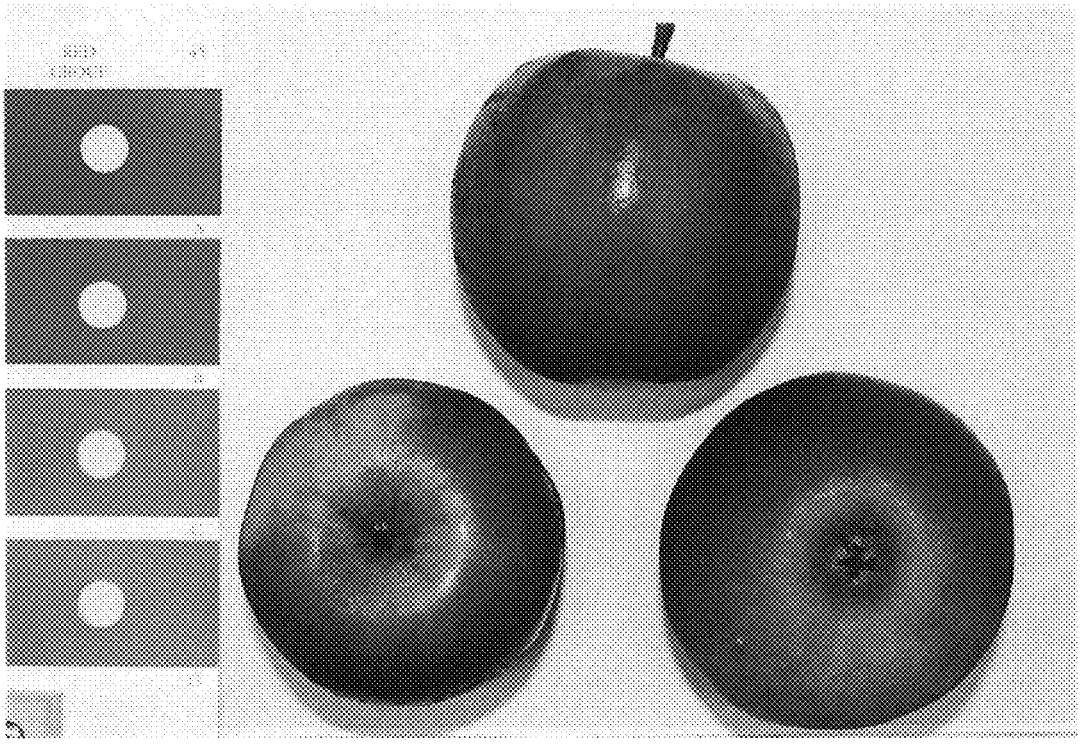

Latin name of the genus and species of the plant claimed: *Malus domestica* Borkh.

Variety denomination: 'KIZURI'.

PRIORITY CLAIM

This application claims priority under 35 U.S.C. §119(f) to European Community Plant Variety Office Application No. 2014/3424 filed Dec. 15, 2014.

BACKGROUND OF THE INVENTION

The present invention relates to a new and distinct variety of Apple tree, botanically known as *Malus domestica* Borkh. of the Rosaceae family, and hereinafter referred to by the variety denomination 'KIZURI'.

The new *Malus* variety is a product of a controlled breeding program conducted by the inventors, Inge De Wit, Hendrik Eyssen, Johan Keulemans, Johan Nicolaï and Paul Van Laer in Belgium. The objective of the breeding program was to develop a new *Malus* variety with crisp and juicy flesh, as well as good storage capacity and shelf life.

The new *Malus* variety originated from a cross made by the inventors in 1990 in Belgium. The female or seed parent is the *Malus domestica* variety designated 'GOLDEN DELICIOUS' (unpatented). The male or pollen parent is the *Malus domestica* variety designated 'NY75413-30' (unpatented). The new *Malus* variety was discovered and selected by the inventors within the progeny of the stated cross in a controlled environment in 2001 in Belgium.

Asexual reproduction of the new *Malus* variety by grafting onto rootstocks was first performed in the winter of 2002-2003 in Belgium, and has demonstrated that the combination of characteristics as herein disclosed for the new variety are firmly fixed and retained through successive generations of asexual reproduction. The new variety reproduces true to type.

BRIEF DESCRIPTION OF THE INVENTION

The following traits have been repeatedly observed and are determined to be unique characteristics of 'KIZURI' which in combination distinguish this Apple tree as a new and distinct variety:

1. very aromatic fruit;
2. sweet fruit;
3. fruit with a solid, vibrant red flush;
4. very firm fruit with dense texture; and
5. very good storability.

In comparison to the parental varieties, 'GOLDEN DELICIOUS' (unpatented) and 'NY75413-30' (unpatented), 'KIZURI' differs primarily in the traits listed in Table 1.

TABLE 1

| Trait | New Variety 'KIZURI' | Female Parent 'GOLDEN DELICIOUS' (unpatented) | Male Parent 'NY75413-30' (unpatented) |
|---|---|---|---|
| Fruit: hue of over color | red | none | dark red |
| Fruit: shape | globose | oblong | oblate |
| Fruit: taste | very sweet | slightly sweet | astringent |
| Fruit: aroma | strong | low | |
| Fruit: time for harvest | 10 days after Golden | — | same as Golden |
| Fruit: firmness | high | medium | |
| Fruit: size | large | medium | very large |

Of the many commercial varieties known to the present inventor(s), the most similar in comparison to the new *Malus* variety 'KIZURI' is the *Malus* variety 'Liberty' (unpatented), in the following characteristics described in Table 2:

TABLE 2

| Characteristic | New Variety 'KIZURI' | Comparison Variety 'LIBERTY' (unpatented) |
|---|---|---|
| Fruit: ribbing | moderate | strong |
| Fruit: bloom of skin | moderate | absent |
| Fruit: pattern of over color | only solid flush | solid flush with weakly defined stripes |
| Fruit: lenticels | present, but not very noticeable | eye-catching |

BRIEF DESCRIPTION OF THE PHOTOGRAPHS

The accompanying photographs illustrate the overall appearance of the new *Malus* variety 'KIZURI' showing the colors as true as is reasonably possible with colored reproductions of this type. Colors in the photographs may differ slightly from the color values cited in the detailed botanical description, which accurately describe the color of 'KIZURI'.

FIG. 1—shows a close-up view (side, top and bottom) of mature fruit of 'KIZURI'.

Figure 2:
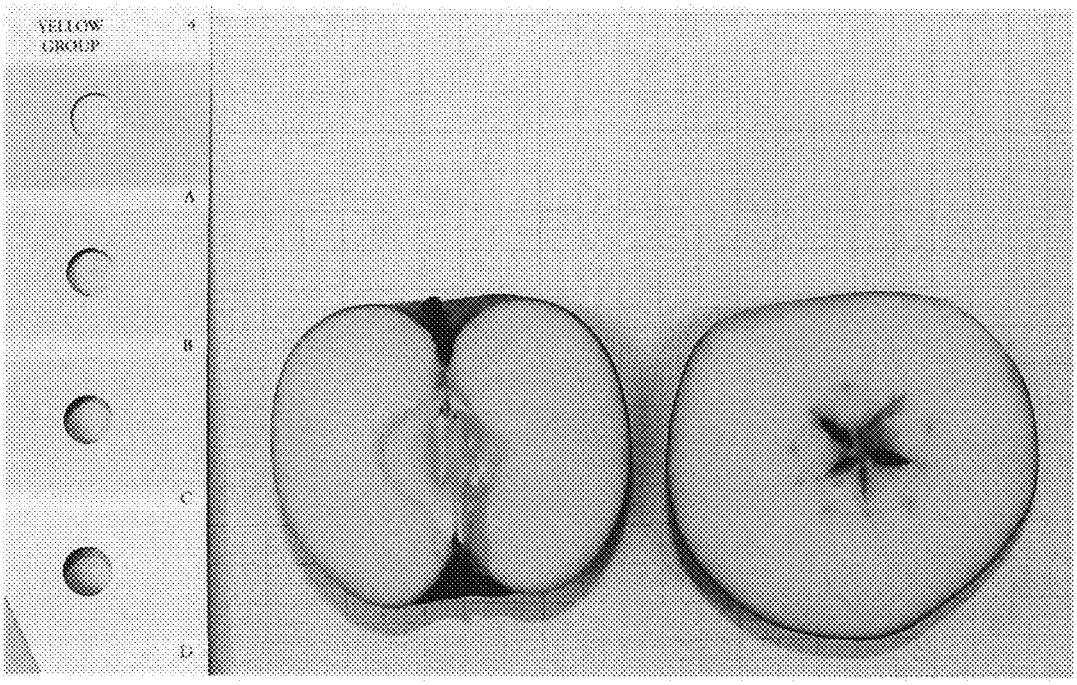

FIG. 2—shows dissection views of mature fruit of 'KIZURI'.

Figure 3:
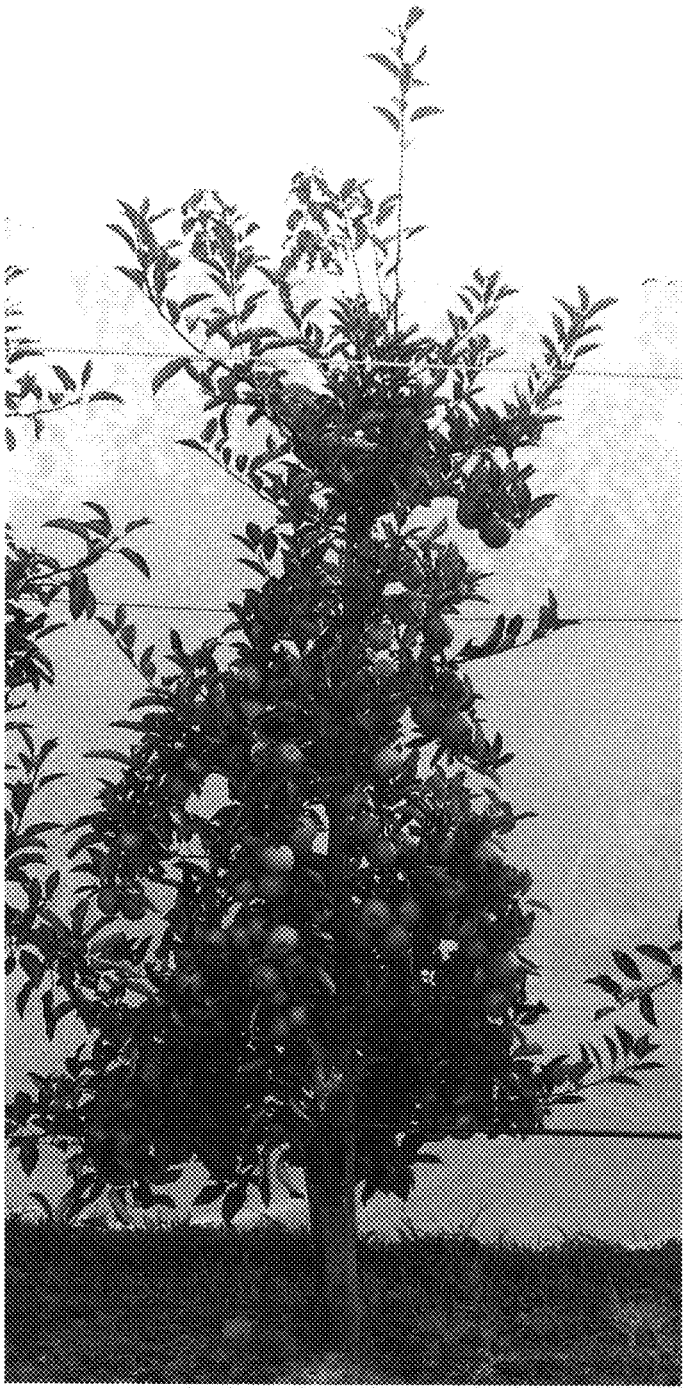

FIG. 3—shows a fruit-bearing tree of 'KIZURI', at 12 years of age.

Figure 4:
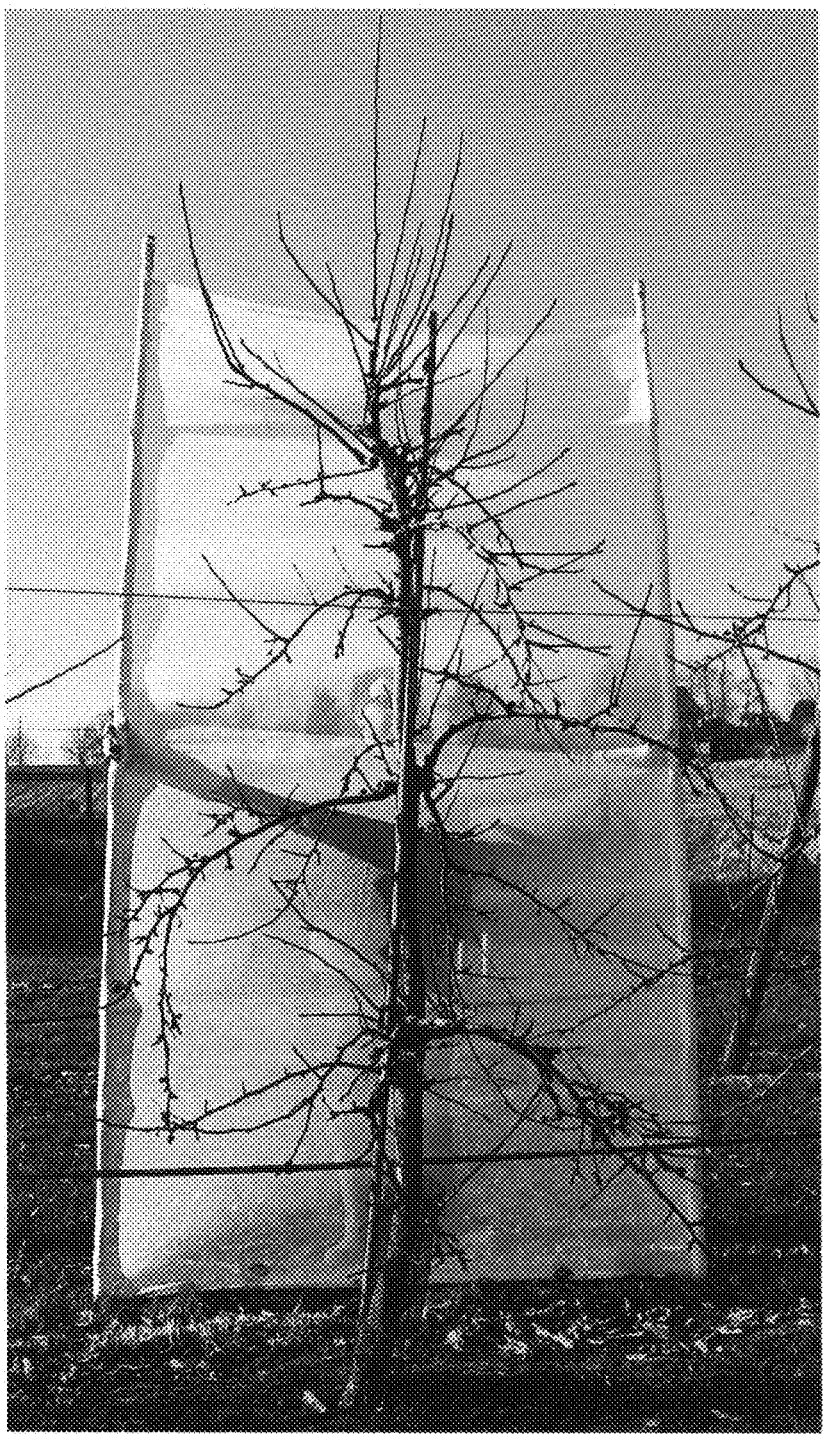

FIG. 4—shows a dormant tree of 'KIZURI', at 12 years of age

Figure 5:
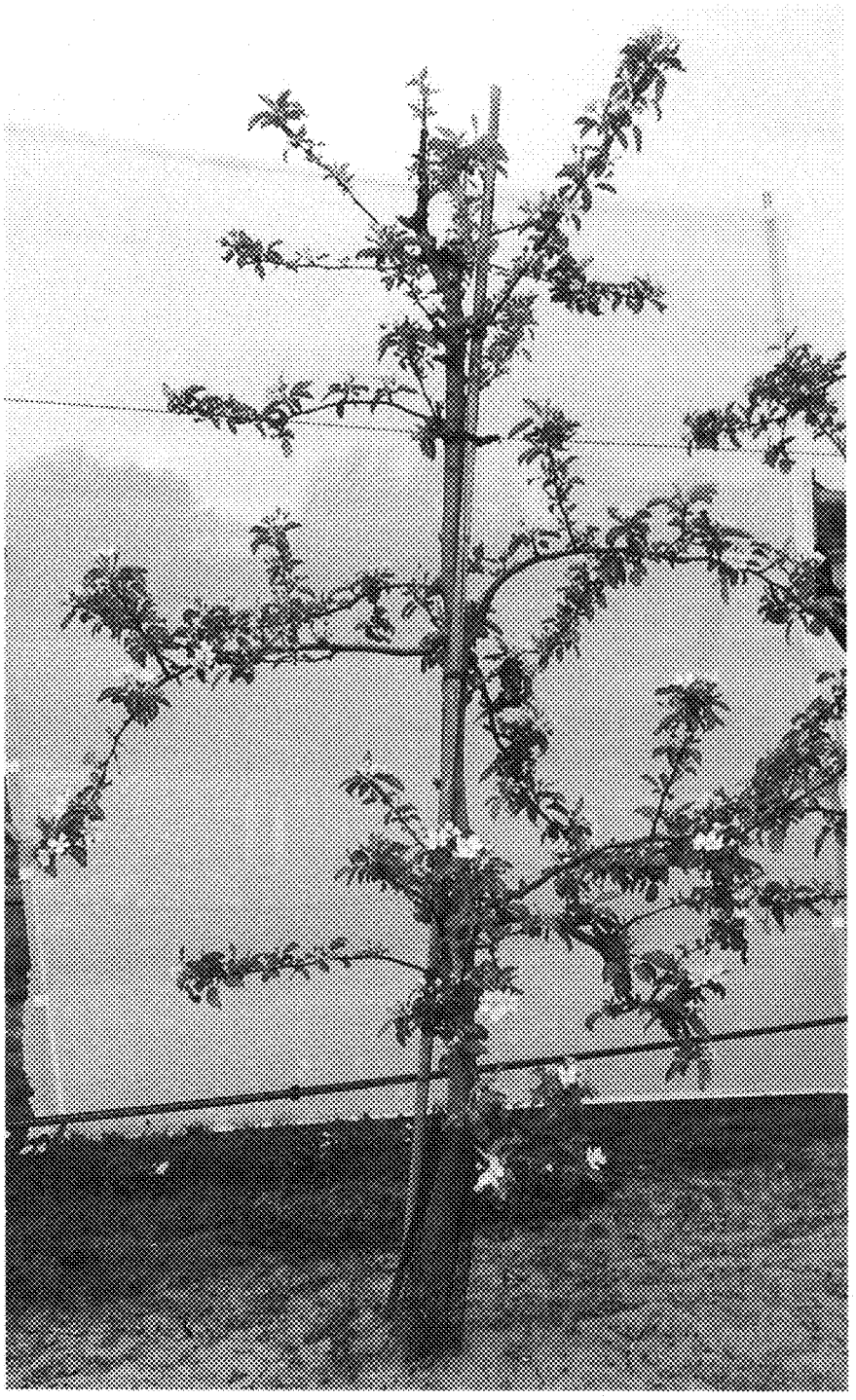

FIG. 5—shows a blooming tree of 'KIZURI', at 12 years of age.

Figure 6:
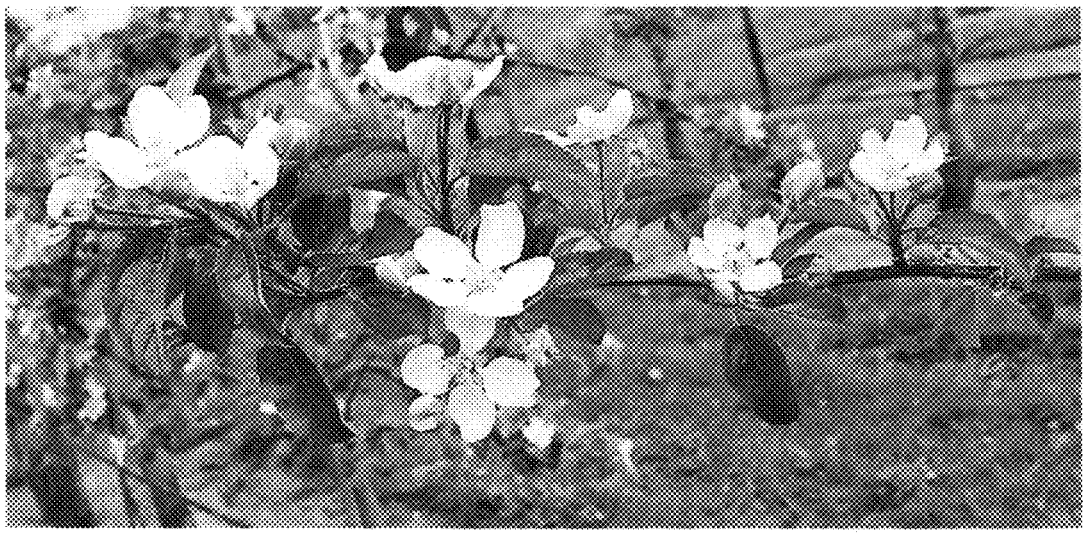

FIG. 6—shows inflorescence of 'KIZURI'.

Figure 7:
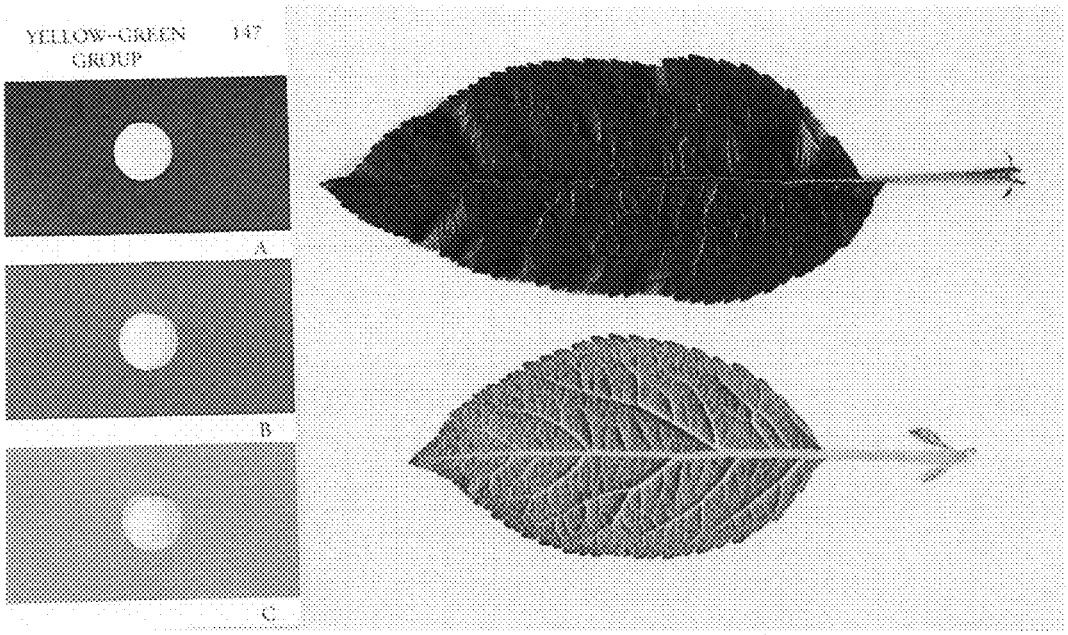

FIG. 7—shows the upper surface (top) and under surface (bottom) view of leaves of 'KIZURI'.

Figure 8:
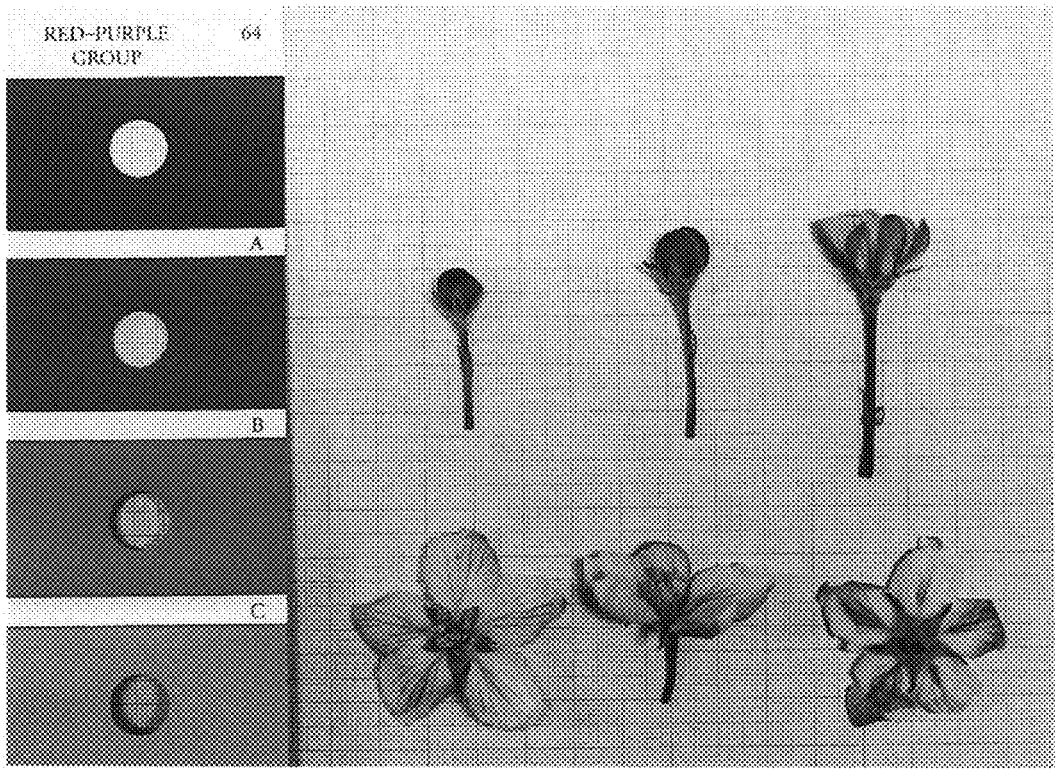

FIG. 8—shows different stages of development of the flowers and the (from left to right) top, side and bottom view of a fully expanded flower of 'KIZURI'.

Figure 9:
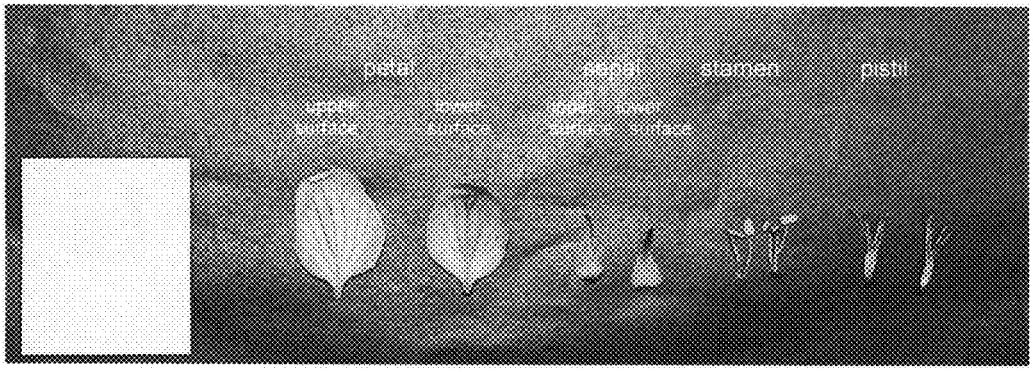

FIG. 9—shows different parts of a flower of 'KIZURI' (from left to right: upper and lower surface of petal, upper and lower surface of sepal, stamen, pistil).

DETAILED BOTANICAL DESCRIPTION

The new *Malus* variety 'KIZURI' has not been observed under all possible environmental conditions. The phenotype of the new variety may vary with variations in environment such as temperature, light intensity, and day length without any change in the genotype of the Apple tree.

The aforementioned photographs, together with the following observations, measurements and values describe trees of 'KIZURI' as grown in Rillaar, Belgium, under conditions which closely approximate those generally used in commercial practice.

Unless otherwise stated, the detailed botanical description includes observations, measurements and values based on 12 years old 'KIZURI' trees grown in Rillaar, Belgium from 2004 to 2015. Quantified measurements are expressed as an average of measurements taken from a number of trees of 'KIZURI'. The measurements of any individual tree, or any group of trees, of the new variety may vary from the stated average.

Color references are made to The Royal Horticultural Society Colour Chart (R.H.S.), (4$^{th}$ edition, 2001), except where general colors of ordinary significance are used. Color values were taken under daylight.

All of the trees of 'KIZURI', insofar as they have been observed, have been identical in all the characteristics described below.

Classification:

*Botanical.*—*Malus domestica.*

Parentage:

*Female or seed parent.*—*Malus* variety designated 'GOLDEN DELICIOUS' (unpatented).

*Male or pollen parent.*—*Malus* variety designated 'NY75413-30' (unpatented).

Propagation: Grafting onto rootstocks.

Growing conditions:

*Light intensities.*—Full sunlight.

*Temperature.*—During day, grown in range of 2° C. to 23° C., and during evening, grow in range of −5 ° C. to 13° C. (based on the average month temperature).

Tree:

*Age.*—Observed trees were 12 years old.

*Vigor.*—Medium to strong.

*Form.*—Ramified, spreading.

*Habit.*—A medium-sized tree with one trunk and 9+/−3 leader(s); main branches spreading; crown symmetrical.

*Branching habit.*—Main branches angle is 81+/−25° with respect to trunk if allowed to grow naturally.

*Density.*—About 2200 trees per hectare.

*Cropping behavior.*—Normal beginning production; medium to high productivity; medium to abundant flowering; little biennial bearing.

*Type of bearing.*—On long shoots.

*Production.*—About 16.9 kg/tree in 2013.

*Size at maturity.*—Height: About 262+/−11 cm. Spread: About 165+/−22 cm.

*Trunk.*—Height (up to leaders): About 92+/−12 cm. Diameter: About 9+/−2 cm. Texture: rough. Bark color: Primarily RHS 197C, with underbark RHS 166C. Trunk Lenticels: Length: About 8.0+/−2.9 mm. Width: About 1.3+/−0.3 mm. Color: RHS 161B. Density: About 2.8+/−0.9 n° per cm$^2$.

*Branches.*—Number per tree: About 74+/−25. Length: maximum 94+/−18 cm; minimum 6+/−3 cm. Diameter (at 2 years): About 19+/−4 mm. Surface texture: slightly rough. Pubescence: none. Color: Mature (after about 3 year old): RHS 200B. New Growth: RHS 166A. Internode length: About 35+/−9 mm. Internode diameter: About 9+/−2 mm. Branch lenticels: Length: About 2.9+/−0.8 mm. Width: About 1.1+/−0.2 mm. Color: RHS 161C. Density: About 4.3+/−1.7 n° per cm$^2$.

*Spur.*—Present: Yes. Distance between each spur: On the 2 and 3 year old branches, the distance is about 3+/−1 cm.. Diameter of each spur: About 5+/−1 mm. Number of fruit per spur: About 1.4+/−1.1.

Foliage:

*Arrangement.*—Alternate, simple, petiolated.

*Lamina.*—Size: Length: About 103+/−15 mm (fully expanded leaf). Width: About 55+/−7 mm (fully expanded leaf). Length/width ratio: 1.9+/−0.2. Overall Shape: obtuse, petiolated. Base shape: obtuse. Apex shape: acute. Margin: biserrate. Texture: Upper surface: smooth, glabrous. Under surface: smooth, medium pubescence (white). Attitude in relation to shoot: upwards. Color (mature leaves): Upper surface: RHS 147A. Under surface: RHS 138B. Color (immature leaves): Upper surface: RHS 143B. Under surface: RHS 143C.

*Venation*.—Type: pinnate. Color: RHS 144D.

*Petiole*.—Length: About 33+/−7 mm. Diameter: About 1.8+/−0.2 mm. Texture: smooth, medium pubescence (white). Color: RHS 144B (upper surface), RHS 144C (lower surface), RHS 59B (at the petiole base, upper and lower surface).

*Stipule*.—Arrangement: free standing. Length (distance of stipules from basal attachment of petiole): About 6.5+/−1.7 mm. Width: About 1.5+/−0.5 mm.

Inflorescence:

*Blooming time*.—Early to medium (after Idared and Boskoop, before Jonagored).

*Blooming period*.—About 1 week.

*Fragrance*.—Slight.

*Type*.—Corymb.

*Number of flowers per inflorescence*.—About 4.8+/−0.9.

*Inflorescence size*.—Diameter: About 86+/−9 mm. Depth: About 57+/−6 mm.

*Buds*.—Terminal Buds: Number per spur: About 1. Shape: a cone with an ellipsoidal base. Length: About 10.3+/−2.3 mm. Width: About 5.2+/−0.8 mm. Texture: smooth, high pubescence. Color: Apex RHS N186B, and base RHS 187A. Scales: Number: About 7.1+/−2.0. Overall shape: triangular, folded double around bud. Apex shape: 3 blunt points. Base shape: straight, fully grown together at base. Color: Upper: RHS 187A. Lower: RHS 151B.

*Lateral buds*.—Number per spur: About 3.9+/−1.9. Shape: a cone with an ellipsoidal base. Length: About 5.8+/−1.6 mm. Width: About 3.5+/−0.5 mm. Texture: smooth, slight pubescence at apex. Color: Apex RHS 187B, and base RHS N186D. Scales: Number: About 5.4+/−0.9. Overall shape: triangular, folded double around bud. Apex shape: acute. Base shape: straight, fully grown together at base. Color: Upper: RHS N186C. Lower: RHS 151D.

*Petals*.—Arrangement: intermediate. Number per flower: 5. Size: Length: About 21+/−3 mm. Width: About 16+/−2 mm. Length/width ratio: 1.3+/−0.1. Overall shape: ovate. Apex shape: rounded. Base shape: rounded. Texture (upper surface): smooth, no hairs. Texture (lower surface): smooth, no hairs. Margin: entire. Color (upper surface): Apex RHS 69D, RHS 64D veined; base RHS 69D. Color (lower surface): Apex RHS 69D, RHS 64C veined; base RHS 69D.

*Sepals*.—Number per flower: 5. Size: Length: About 9.0+/−1.1 mm. Width: About 4.5+/−0.5 mm. Length/width ratio: 2.0+/−0.3. Overall shape: triangular. Apex shape: aristate. Base shape: truncate. Texture (upper surface): smooth, hairy. Texture (lower surface): smooth, hairy. Margin: entire. Color (upper surface): Apex RHS 178B, base RHS 144B. Color (lower surface): Apex RHS 178B, base RHS 143B.

*Pedicel*.—Length: 27+/−5 mm. Diameter: 1.6+/−0.2 mm. Texture: smooth, hairy (white hairs). Color: RHS 144B; a line of RHS 178B.

Fruit:

*Keeping quality*.—It can be stored in cold temperature conditions for up to 6 months (normal atmosphere). It has a shelf life of about 5 weeks.

*Maturity when described*.—Ripe for eating.

*Maturity period after full bloom*.—About 5.5 months after full bloom.

*Date of first and last picking* (*harvest*).—First 2 weeks of October.

*Type*.—Pome.

*General shape*.—Oblong.

*Average weight*.—About 266+/−44 g.

*Fruit size*.—Average height: About 74+/−5 mm. Average diameter (at widest point): About 84+/−4 mm. Position of maximum diameter: middle. Height/thickness ratio: 0.9+/−0.1.

*Stem*.—Length: About 23+/−5 mm. Diameter: About 2.5+/−0.4 mm. Color: RHS 199A, RHS 151A (both full length).

*Stalk cavity*.—Depth: About 15.5+/−3.2 mm. Width: About 34.3+/−3.7 mm.

*Eye basin*.—Depth: About 12.3+/−2.7 mm. Width: About 32.8+/−4.7 mm. Crowning at calyx end: weak to moderate. Position of sepals: Half-closed. Calyx tube: closed to partly open.

*Skin*.—Thickness: 0.2+/−0.1 mm. Texture: tough. Bloom: absent. Greasiness: absent. Firmness (at picking time): 7.6+/−0.9 kg/cm$^2$. Overcolor color: RHS 45A. Percentage of skin surface with overcolor color: About 50 to 75%. Pattern of overcolor: only solid flush. Intensity of overcolor: medium to low. Ground color: RHS 1C. Skin Lenticels: Length: About 1.4+/−0.2 mm. Width: About 1.1+/−0.2 mm. Color: RHS 197D. Density: About 3.0+/−2.0 n° per cm$^2$.

*Flesh*.—Color: RHS 4D. Texture: firm, crisp and juicy. Aroma: strong. Eating quality: excellent. Sugar content (at picking time): 14.5+/−1.4 Brix. Acidity/Starch (at picking time) 5.6+/−0.3 g/l malic acid. Core: Symmetry of core: round. Distinctness of core lines: weak. Locules: Number (per fruit): 5. Length: About 10+/−1 mm. Width: About 4+/−1 mm. Form: teardrop shape.

Seeds:

*Number per fruit*.—About 5.4+/−3.8.

*Number per locule*.—About 1.2+/−0.8.

*Shape*.—Teardrop shape.

*Length*.—About 9.6+/−1.1 mm.

*Width*.—About 5.0+/−0.4 mm.

*Texture*.—Smooth.

*Color*.—RHS 166A and RHS 166B.

Reproductive organs:

*Androecium*.—Stamen: Number per flower: 19.2+/−1.1. Length: About 8.5+/−1.9 mm. Anther: Length: About 3.1+/−0.4 mm. Color: RHS 10C. Filaments: Length: About 7.3+/−1.5 mm. Color: RHS N155C. Pollen: Amount: high. Color: RHS 6B. Pollination Requirements: cross pollination.

*Gynoecium*.—Pistils: Quantity: 5. Length: About 14.0+/−1.2 mm. Color: RHS 144C. Stigmas: Color: RHS 144C. Ovary: Length: About 4.7+/−0.7 mm. Width: About 1.7+/−0.5 mm. Color: RHS 144C.

Use: Fresh market.

Disease/pest resistance: No known resistance to pests and diseases.

Disease/pest susceptibility: Tolerant to canker (*Nectria galligena*), powdery mildew (*Podosphaera leucotricha*) and fire blight (*Erwinia amylovora*); susceptible to scab (*Venturia inaequalis*) and wooly apple aphid (*Eriosoma lanigerum*).

Winter hardiness: Tolerant to temperatures down to −10° C. without observed damage to wood and buds of dormant Apple trees.

Drought/heat tolerance: Tolerant to temperatures up to 40° C., growth is limited by drought periods without irrigation.

Shipping/storage characteristics: Not sensitive to bruising; good storability under ULO-conditions (maintains high quality for up to 6 months).

We claim:

1. A new and distinct variety of *Malus domestica* apple tree named 'KIZURI', as illustrated and described herein.

* * * * *